United States Patent
Ulrici

(10) Patent No.: US 10,521,935 B2
(45) Date of Patent: *Dec. 31, 2019

(54) METHOD FOR CREATING AN IMAGE FROM A 3D VOLUME

(71) Applicant: Sirona Dental Systems GmbH, Bensheim (DE)

(72) Inventor: Johannes Ulrici, Darmstadt (DE)

(73) Assignee: Sirona Dental Systems GmbH, Bensheim (DE)

(*) Notice: Subject to any disclaimer, the term of this patent is extended or adjusted under 35 U.S.C. 154(b) by 0 days.

This patent is subject to a terminal disclaimer.

(21) Appl. No.: 15/589,979

(22) Filed: May 8, 2017

(65) Prior Publication Data
US 2017/0243381 A1 Aug. 24, 2017

Related U.S. Application Data

(63) Continuation of application No. 13/820,442, filed as application No. PCT/EP2011/065065 on Sep. 1, 2011, now Pat. No. 9,652,873.

(30) Foreign Application Priority Data

Sep. 1, 2010 (DE) .......................... 10 2010 040 096

(51) Int. Cl.
*G06T 11/00* (2006.01)
*A61B 6/03* (2006.01)
(Continued)

(52) U.S. Cl.
CPC ............ *G06T 11/008* (2013.01); *A61B 6/032* (2013.01); *A61B 6/14* (2013.01); *G06T 15/08* (2013.01); *A61B 6/466* (2013.01); *G06T 2210/41* (2013.01)

(58) Field of Classification Search
CPC combination set(s) only.
See application file for complete search history.

(56) References Cited

U.S. PATENT DOCUMENTS

| 5,179,579 A | 1/1993 | Dove et al. |
| 6,064,391 A | 5/2000 | Sano et al. |

(Continued)

FOREIGN PATENT DOCUMENTS

| DE | 10108295 A1 | 9/2002 |
| DE | 10196737 T1 | 9/2003 |

(Continued)

OTHER PUBLICATIONS

Jackowski, C., et al. "Ultra-high-resolution dual-source CT for forensic dental visualization-discrimination of ceramic and composite fillings", International Journal of Legal Medicine, vol. 122, No. 4, Jul. 1, 2008, pp. 301-307.

(Continued)

*Primary Examiner* — Zhitong Chen
(74) *Attorney, Agent, or Firm* — Venable LLP

(57) ABSTRACT

The invention relates to a method for creating a virtual dental image from a 3D volume (1) comprising volumetric image data. Firstly, a sub-volume (8, 12, 15, 18) of the 3D volume (1) is defined and then a virtual projection image (30, 41) is generated for said sub-volume (8, 12, 15, 18) from a specific X-ray imaging direction (11) by computation of the volumetric image data in said X-ray imaging direction (11).

24 Claims, 3 Drawing Sheets

(51) Int. Cl.
*A61B 6/14* (2006.01)
*G06T 15/08* (2011.01)
*A61B 6/00* (2006.01)

(56) References Cited

U.S. PATENT DOCUMENTS

| | | | |
|---|---|---|---|
| 6,190,042 B1 | 2/2001 | Dove et al. | |
| 7,010,153 B2 | 3/2006 | Zimmermann | |
| 8,320,522 B2 | 11/2012 | Ulrici et al. | |
| 2003/0053712 A1* | 3/2003 | Jansson | G06K 9/40 |
| | | | 382/275 |
| 2004/0066877 A1* | 4/2004 | Arai | A61B 6/0478 |
| | | | 378/4 |
| 2006/0232608 A1* | 10/2006 | Riaz | G06T 11/008 |
| | | | 345/642 |
| 2008/0085041 A1* | 4/2008 | Breeuwer | G06T 5/006 |
| | | | 382/128 |
| 2008/0182220 A1* | 7/2008 | Chishti | A61C 7/00 |
| | | | 433/24 |
| 2008/0267343 A1 | 10/2008 | Sukovic et al. | |
| 2011/0033026 A1 | 2/2011 | Ulrici et al. | |
| 2011/0109630 A1 | 5/2011 | Breuer et al. | |
| 2013/0064440 A1* | 3/2013 | Wiemker | G06T 15/08 |
| | | | 382/131 |

FOREIGN PATENT DOCUMENTS

| | | |
|---|---|---|
| DE | 10 2008 008 733 A1 | 8/2009 |
| DE | 10 2008 021 926 A1 | 11/2009 |
| WO | 2009-101123 A1 | 8/2009 |
| WO | WO2009/101123 A1 * | 8/2009 ............... A61B 6/14 |

OTHER PUBLICATIONS

Written Opinion of the International Search Authority dated Mar. 5, 2013, in International Patent Application No. PCT/EP2011/065065.
International Search Report dated Jan. 20, 2013, in International Patent Application No. PCT/EP2011/065065.

* cited by examiner

METHOD FOR CREATING AN IMAGE FROM A 3D VOLUME

TECHNICAL FIELD

The invention relates to a method for creating an image from a 3D volume comprising volumetric image data of a mandibular arch and of teeth.

PRIOR ART

Several methods for creating a virtual three-dimensional X-ray image are disclosed in the prior art. In the method of digital volume tomography (DVT), an X-ray source assembly and a sensor interconnected by an axis are moved around the head of the patient in a defined plane. Projection images are generated from various positions along this circular path, and in the next step a three-dimensional volume is computed from said projection images. The 3D volume can then be displayed by application software on a monitor. In the method of computed tomography (CT), the image is formed on the basis of continuous imaging of the projection from different directions. Usually, the computed 3D reconstructions are composed of individual slices according to the sliced imaging technique, which slices extend through the object at right angles thereto. In this way, the X-ray absorption value can be defined for each of the volume elements of the object, the so-called voxels.

DE 101 08 295 A1 discloses a method for identifying objects, particularly teeth, and a system for effecting the same, based on a digitized X-ray image, in which method regions in the object are delimited by segmentation and/or edge detection using image-processing algorithms, and these regions are associated by computation with parameters of the X-ray apparatus and of the patient, where appropriate, to give further parameters. Furthermore, a method is disclosed in which the objects are manually or automatically specified, and, in one step, the object is selected for which more information is to be saved, retrieved, or deleted, and a reference relating to the object is saved in a further step, which reference makes it possible to specify the information to be displayed.

The methods of edge detection and segmentation are applied to the image data of the digitized X-ray image with the assistance of a computer, and the defined edges and segments are grouped by the so-called clustering technique.

U.S. Pat. No. 5,179,579 discloses a method of displaying intraoral X-ray images. The intraoral X-ray images are produced, digitized, and displayed together with an icon of that portion of the anatomy, from which the X-ray image has been taken. The images of the anatomical sites are displayed with the respective icon in normal anatomical relation to each other on a monitor. The icon is used by the user in order to select the respective X-ray image of the anatomical site. A miniaturized image of the dentition, of a row of teeth, or of the individual teeth may be used, for example, as the icon.

U.S. Pat. No. 6,190,042 B1 discloses a device for creating improved intraoral X-ray images. The device comprises a bite block, a guiding rod, an aiming ring, and an additional ring. The bite block comprises a film holder disposed at right angles to the top surface of the bite block. The guiding rod is connected to the bite block. The device guaranties a predefined distance between the film in the film holder and the external ring.

A drawback of the devices and methods disclosed in the prior art is that the generation of the intraoral image requires an elaborate device to be positioned and secured in the mouth of the patient, which device mostly comprises a bite block for securing the device, while an X-ray film or a digital X-ray sensor is disposed in the form of imaging means on this device in the oral cavity of the patient. Positioning of this device is difficult to carry out on account of the fact that the patient alters the position of the device relative to the upper jaw while biting on the block and that the distance of the imaging element from the teeth is unknown.

In the case of a series of several intraoral images, gaps may result between the individual images due to the imprecise positioning of the device, and thus the oral cavity of the patient is incompletely imaged.

Furthermore, the imaging volume of the intraoral images with respect to the teeth in the imaging direction is not known.

DE 10 2008 008 733 A1 discloses a method for creating a tomogram, for which purpose, in particular, a dental X-ray panoramic tomogram is produced from a digital 3D volume showing X-ray absorption values, and X-rays are passed virtually through the 3D volume, as the object to be imaged, by means of a virtual X-ray source, and the resulting virtual image is recorded by a virtual detector. The virtual X-ray source and the virtual detector are moved virtually past the object being imaged to form a sharp layer having a blurred region.

The width of the virtual detector, the broadening of the virtual fan beam and the simulated speed of rotation of the virtual X-ray source and the virtual detector can be altered in order to control the thickness and position of the imaged sharp layer. In one embodiment, a defined sub-region, the extent of which corresponds to the sharp layer, is selected from the 3D volume, and X-rays are passed virtually through the sub-region at right angles to the contour of the sub-region to form a panoramic image.

A drawback of this method is that the virtually generated panoramic image, unlike an intraoral projection image, represents a distorted image of the entire dental arch and thus makes it difficult to diagnose specific findings.

It is therefore an object of this invention to generate a two-dimensional projection image for a defined imaging volume.

SUMMARY OF THE INVENTION

It is one object of the present invention to provide a method for creating a virtual dental image from a 3D volume comprising volumetric image data. Firstly, a sub-volume is specified from the 3D volume. A virtual projection image is generated for this sub-volume from a defined X-ray imaging direction by computing the volumetric image data in this X-ray imaging direction.

The 3D volume can be a three-dimensional X-ray image generated by means of any desired three-dimensional radiographic procedures such as DVT or CT, and the volumetric image data can be composed of voxels having X-ray absorption values. The 3D volume can also be imaged by means of other imaging techniques such as MRI. The 3D volume can include the entire dental arch including the teeth, or a portion thereof. The volumetric image data of the 3D volume can be composed of voxels, vector elements, or a combination of voxels and vector elements. The volumetric image data can also be composed of point clouds containing vector elements. A defined sub-volume having any desired basal surface and a defined thickness in the X-ray imaging direction is selected from this 3D volume. In a further step, a virtual projection image is generated for this selected sub-volume by computing the volumetric image data such as voxels or vector elements in the X-ray imaging direction. This results in a virtual projection image of the selected sub-volume, which virtual projection image corresponds to an intraoral X-ray image of a specific region of the dental arch. The volumetric image data can be computed in the X-ray imaging direction, for example, by summation of the individual volumetric image data such as voxels or vector elements disposed one behind the other in the X-ray imaging direction. The volumetric image data can alternatively be computed by means of integration following the application of a defined function to the voxels disposed in the X-ray imaging direction.

A defined function can be applied to the volumetric image data prior to computation of the volumetric image data in order to weight the volumetric image data in the X-ray imaging direction in such a way that specific portions, such as carious regions, that are of significance to the evaluation, are highlighted, while less weight is given to other portions, such as a filling, that are of no significance to the evaluation. Such a function can be applied, for example, to the gray tones of the individual elements of the volumetric image data.

The 3D volume can be composed of voxels that represent volume elements of the object imaged. Any three-dimensional dental image can be used as the 3D volume, for example a three-dimensional X-ray image, namely a digital volume tomogram or a computed tomogram comprising voxels having X-ray absorption values in the form of gray tones or a magnetic resonance tomogram comprising voxels representing volume elements of the tissue imaged. The 3D volume can alternatively be a three-dimensional ultrasonogram.

When the projection image is generated, the volumetric image data can be computed by summation of the X-ray absorption values in the X-ray imaging direction with the virtual X-ray imaging direction being parallel across the entire basal surface or in the form of a conical fan as an extension of virtual X-rays emanating from a virtual X-ray source.

The basal surface may be of any desired shape, for example, a circle, a rectangle, or a defined contour of the object to be imaged.

The sub-volume may be of any other basic geometric shape, such as a tetrahedron, or it may have the shape of a segmented sub-volume.

An optimal projection image is generated having a basal surface in the form of a rectangle in a parallel X-ray imaging direction so that the selected sub-volume has the shape of a cuboid.

The projection image should have dimensions that are equal to the size of a conventional intraoral image created with single-tooth radiographs, namely a width ranging from 15 mm to 30 mm and a height ranging from 25 mm to 40 mm.

One advantage is that the patient need not again be exposed to x-rays in order to generate projection images. The projection images, such as intraoral X-ray images of specific regions, can be generated from the existing three-dimensional image data of the 3D volume.

A further advantage is that the sub-volume can be defined precisely by the user with the assistance of a computer and, for example, intraoral X-ray images of individual teeth can be generated.

Yet another advantage is that the sub-volume can be selected such that a region of interest in the 3D volume such as a filling can be excluded virtually in order to compute a projection image that does not contain the portion that has been excluded. This makes it possible to diagnose, for example, secondary caries located under the filling. This method of excluding specific structures can be applied to fillings, dentin layers, tooth enamel structures, etc., which can be excluded virtually following appropriate segmentation.

Advantageously, the 3D volume comprising volumetric image data may be a three-dimensional X-ray image having X-ray absorption values.

Thus the virtual projection image corresponds to a two-dimensional X-ray image created in a defined X-ray imaging direction.

Advantageously, the volumetric image data can be computed by summation of the volumetric image data, such as voxels or vector elements, that are disposed successively along the X-ray imaging direction.

This makes it possible, for example, to compute each pixel of the projection image by summation of the voxels in the X-ray imaging direction with regard to their gray tones.

Advantageously, the volumetric image data may be computed by integration, following the application of a defined function to the elements of the volumetric image data disposed in the X-ray imaging direction.

This is a further alternative to computing the volumetric image data and permits different weighting of the elements according to a defined function. This function can be designed such that specific portions are invisible or only weakly visible, while more weight is given to the portions of diagnostic significance.

Advantageously, the sub-volume may be defined manually or automatically with the assistance of a computer.

The sub-volume can be defined manually by a user by the use of input devices. The sub-volume can alternatively be defined automatically using a computer and software for processing image data and using conventional image-processing techniques such as the identification or segmentation of defined sub-objects, such as teeth or jawbones.

Advantageously, the sub-volume can be defined automatically with reference to a segmented sub-object, and the external contour of the sub-volume is defined so as to correspond to an external contour of the segmented sub-object.

A conventional method of pattern recognition can be used for segmentation purposes. By this means a volume includes only the sub-object to be diagnosed so that the adjoining tissue, such as gums and the jawbone, is ignored and diagnosis is thus facilitated.

Advantageously, the external contour of the sub-volume can be defined manually such that it corresponds to the external contour of a characteristic sub-object.

This makes it possible for the user to define the external contour of the sub-volume manually using input devices according to the external shape of the sub-object to be diagnosed, such as a tooth or a group of teeth.

Advantageously, the teeth and/or the dental arch can be identified first from the 3D volume. Then the position and orientation of the teeth and/or the dental arch in the 3D volume are defined in order to define the sub-volume and the X-ray imaging direction for the purpose of generating the virtual projection image.

The teeth and the dental arch can be identified from the 3D volume either automatically with the assistance of a computer or manually by a user employing input devices, such as a mouse and a keyboard and a display device such as a monitor. In the automatic identification or segmentation, use is made of conventional methods for pattern recognition in which objects are segmented and the relationship between the objects is sought. The method of pattern recognition can include the following steps: preprocessing, feature extraction, feature reduction, and classification of features. During preprocessing, undesirable or insignificant components of the image data are removed. During feature extraction, defined features are extracted from the image data by comparing them with known patterns from a database such as a database of characteristic teeth. Automatic comparison is carried out using transformation functions and scaling, a comparative factor being computed by calculating the variance between a pattern from the image data and an expected pattern from the database. Feature reduction involves examination of the features to determine those that are important for classification purposes and those that can be omitted. In particular, the extracted patterns of teeth and the dental arch are of significance for this method, while the remaining extracted features can be disregarded. In the last step of the classification, the essential features recognized, such as teeth and characteristic shapes of the dental arch, are split up into appropriate classes, such as incisors, molar teeth, tooth roots, and jawbones.

Feature extraction involves the use of known methods such as raster analysis, cluster analysis, and pattern matching.

Advantageously, the sub-volume can be defined in the form of a prism having an arbitrary basal surface and a defined thickness in the X-ray imaging direction.

The sub-volume can be defined automatically with the assistance of a computer with reference to specific recognized objects such as teeth or groups of teeth, or it can be input manually by the user. Firstly, a basal surface, and then the thickness in the X-ray imaging direction are defined. This results in a geometric prism, and the X-ray imaging direction can extend at right angles to the basal surface.

In this way the sub-volume can be defined such that specific objects, such as teeth or groups of teeth, or specific portions of the jawbone, are disposed in the sub-volume. By defining the thickness, it is possible to delimit the sub-volume such that it contains only the object to be imaged, while other objects, such as a patient's cheek disposed in front of or behind the object to be imaged in the X-ray imaging direction, are not included in the sub-volume and thus do not emerge as disturbing artifacts in the computed projection image.

Advantageously, the virtual projection image can be saved in the form of an intraoral image in application software for the administration of dental X-ray images.

A virtual projection image, created in an X-ray imaging direction oriented lingually or palatally at right angles to the course of the dental arch and having a sub-volume that includes specific teeth, will correspond to an intraoral image and can be saved as such in available application software.

This makes it possible to use the computed projection image for diagnosis in the manner of a conventional intraoral image.

Advantageously, the virtual projection image can be displayed on a display device in the form of a virtual intraoral image.

This makes it possible to display the virtual projection image as a conventional intraoral image on a display device, such as a computer monitor, using available application software.

Advantageously, a plurality of projection images can be generated from different sub-volumes in different X-ray imaging directions according to a predefined schema.

These sub-volumes can be of arbitrary shape. They can have variable thickness and a selected basal surface or they can be defined such that their external contour corresponds to a segmented sub-object, such as a tooth or a group of teeth. The projection images created can alternatively be displayed in a defined arrangement by means of the display device.

This makes it possible to generate a series of a plurality of virtual intraoral images covering the entire oral cavity of the patient.

The series of virtual intraoral images can be generated according to a conventional schema as shown in FIGS. 5A to 5S of U.S. Pat. No. 5,179,579 and disclosed in the relevant portions of the description.

The individual virtual intraoral images of the series can include one or more teeth. A virtual intraoral image of a plurality of teeth also makes it possible to diagnose regions between the teeth.

This enables intraoral images of the individual teeth or groups of teeth to be created in order to improve the diagnosis. Thus a series of intraoral images of the entire oral cavity of the patient (full mouth series) can be generated. Unlike conventional intraoral images created using a film or an intraoral sensor, it is possible to arrange the virtual sub-volumes in a precise manner such that the sub-volumes can adjoin each other without any gaps between them in a series of images, which improves possible diagnosis results.

Advantageously, each sub-volume can include image data comprising volumetric image data of an individual tooth or a group of teeth in the dental arch in order to create separate projection images of an individual tooth or of individual groups of teeth.

Thus a series of projection images of the individual teeth in both of the dental arches can be generated.

The sub-volume may include only portions of teeth, such as half a tooth. The sub-volume may include a tooth and two tooth gaps.

Advantageously, an X-ray imaging direction can be defined for each sub-volume in the palatal direction towards the gums or in the lingual direction towards the tongue, with the individual sub-volumes being directly juxtaposed or partially overlapping each other, so to create a series of projection images of the entire dental arch.

Thus the X-ray imaging direction of the resulting projection images corresponds to the usual orientation of intraoral images, so that the series formed can be used for diagnosis in the same manner as a series of conventional intraoral images.

Advantageously, an X-ray imaging direction can be defined for each sub-volume in the occlusal direction along a tooth axis, with the individual sub-volumes being directly juxtaposed or partially overlapping each other, so as to create a series of occlusal projection images of the entire dental arch.

This makes it possible to effect diagnosis from the occlusal direction of the teeth over the entire dental arch.

Advantageously, the virtual projection images produced from the 3D volume can be arranged automatically so as to include the complete range of teeth disposed in the oral cavity.

This makes it possible to generate a series of intraoral images (full mouth series) so as to include the complete oral cavity of the patient.

Advantageously, the virtual projection image can be equivalent to an intraoral image created by means of an intraoral imaging device comprising an X-ray source assembly and an image receptor, such as an intraoral sensor.

In the case of an X-ray imaging direction extending at right angles to the orientation of the dental arch, the projection image corresponds to a conventional intraoral image of a portion of the dental arch. The virtual projection image can alternatively be created for individual teeth in an X-ray imaging direction extending along the dental arch. Such projection images can be advantageous for the diagnosis of specific findings on the approximal surfaces in an interdental gap.

Advantageously, the 3D volume can be imaged by methods involving digital volume tomography (DVT), computed tomography (CT), three-dimensional ultrasonics, or magnetic resonance imaging (MRI).

Thus a 3D volume is generated which shows high resolution and high imaging quality.

Advantageously, specific physical conditions relevant to conventional intraoral images, such as scattering, the properties of the X-ray source assembly, the X-ray spectrum, or the arrangement of the detector relative to the X-ray source assembly can be allowed for when creating the virtual projection image for the defined sub-volume.

These factors can be simulated, for example, with the assistance of a computer or retrieved from a database comprising factors for different arrangements whilst allowing for different physical conditions.

Thus a conventional intraoral image is replicated in terms of the physical conditions in order to make diagnosis possible in a conventional manner.

Advantageously, specific unwanted sub-objects such as fillings or jawbones can be excluded from the sub-volume when the sub-volume is being defined or they can be allowed for with a lower weighting when computing the volumetric image data, in order to facilitate examination of the sub-objects, such as teeth, included in the sub-volume, for example for secondary caries.

This makes it possible to improve diagnosis of, in particular, secondary caries disposed in most cases between the filling and the tooth substance.

Advantageously, defined system characteristics of a conventional intraoral image, such as the detector efficiency, a detector characteristic or a plurality of detector characteristics, and/or the detector sensitivity in the case of different detectors, can be simulated for the defined sub-volume when the virtual projection image is being generated, and the type of detector, such as a memory foil system, single-tooth radiographs of variable sensitivity, or a digital intraoral sensor, can be selected virtually.

These system characteristics can also be retrieved from a database for different image data.

This makes it possible to simulate system characteristics of specific types of detector in order to imitate as precisely as possible a conventional intraoral image created with this type of detector. The type of detector can be selected by the user virtually using input devices.

BRIEF DESCRIPTION OF THE DRAWINGS

Exemplary embodiments of the invention are shown in the drawings, in which.

DESCRIPTION OF THE EXEMPLARY EMBODIMENTS

Figure 1:
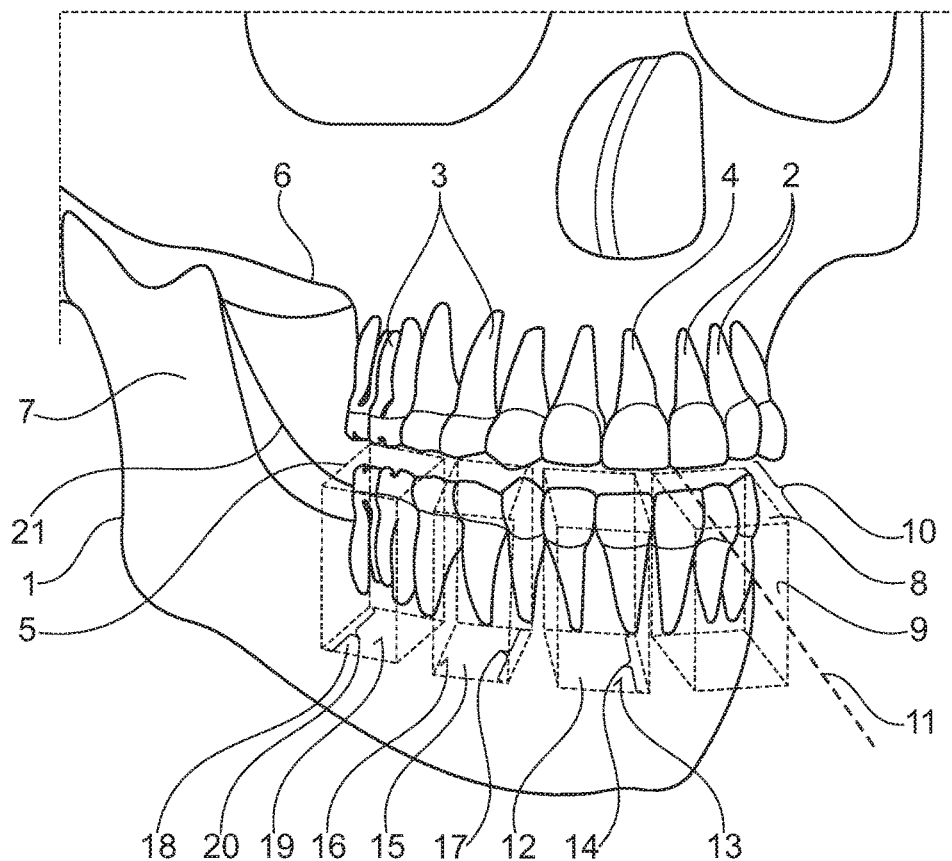
FIG. 1 is a diagrammatical representation of a 3D volume comprising selected sub-volumes.

FIG. 1 is a diagrammatical representation of a 3D volume 1 imaged by means of digital volume tomography (DVT) or computed tomography (CT). The 3D volume 1 is composed of voxels having specific X-ray absorption values. The 3D volume comprises a plurality of structures such as the central incisors 2, the lateral molars 3, and the maxillary arch 4, the mandibular arch 5, the upper jawbone 6, and the lower jawbone 7. The 3D volume 1 is displayed in application software on a computer monitor (not shown in the figure). The 3D volume can be moved and rotated arbitrarily in order to alter the viewing direction of the display. In the first step of the method of the invention, a virtual sub-volume 8 having a specific basal surface 9 and a specific thickness 10 in an X-ray imaging direction 11 is defined. The sub-volume can be defined automatically with the assistance of a computer or manually by a user. When the sub-volume is defined automatically, the individual teeth are identified and classified by means of a conventional method of pattern recognition, and the sub-volume is defined such that specific portions of the dental arch are included therein. When the sub-volume is defined manually, the user can first define the base 9 by means of input devices and then define the thickness of the sub-volume. The sub-volume 8 defined is displayed highlighted in relation to the 3D volume 1 in the application software. The second sub-volume 12 having the basal surface 13 and the thickness 14, the third sub-volume 15 having the basal surface 16 and the thickness 17, and the fourth sub-volume 18 having the basal surface 19 and the thickness 20 are defined accordingly. When the sub-volumes 8, 12, 15, and 18 are defined, the thickness 10, 14, 17, 20 is oriented in an X-ray imaging direction extending at right angles to the course 21 of the lower row of teeth in the palatal direction towards the gums or in the lingual direction towards the tongue. The individual sub-volumes 8, 12, 15, and 18 adjoin each other without gaps therebetween. A two-dimensional virtual projection image corresponding to a conventional intraoral image of the respective portion of the dental arch within the sub-volume is generated from the selected sub-volumes by summation of the X-ray absorption values in the X-ray imaging direction in the second step of the method of the invention with the assistance of a computer using an algorithm. The shape of the sub-volumes 8, 12, 15, and 18 is equivalent to that of a prism having a basal surface 9, 13, 16, 19 and a thickness 10, 14, 17, and 20 respectively.

The projection image generated is saved in the form of a virtual intraoral image in a database in a conventional software application.

Figure 2:
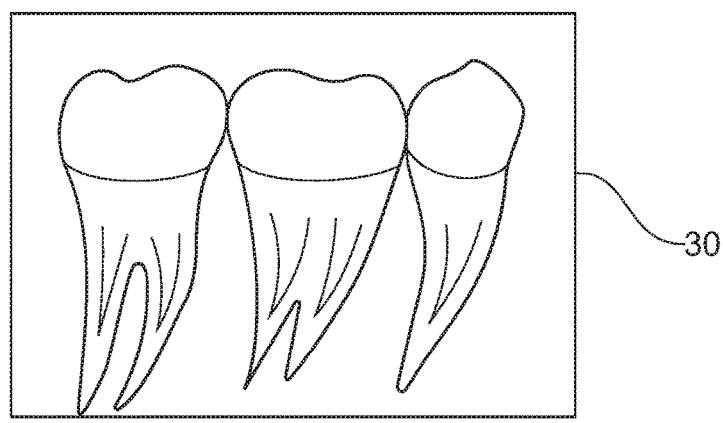
FIG. 2 is a diagrammatical representation of a projection image generated from a sub-volume.

FIG. 2 is a diagrammatical representation of a projection image 30 generated from the fourth sub-volume 18 of the molar teeth of the mandibular arch 5. The virtual projection image 30 corresponds to a conventional intraoral image and is displayed in the software application on a computer monitor and saved accordingly in a database intended for this purpose.

Figure 3:
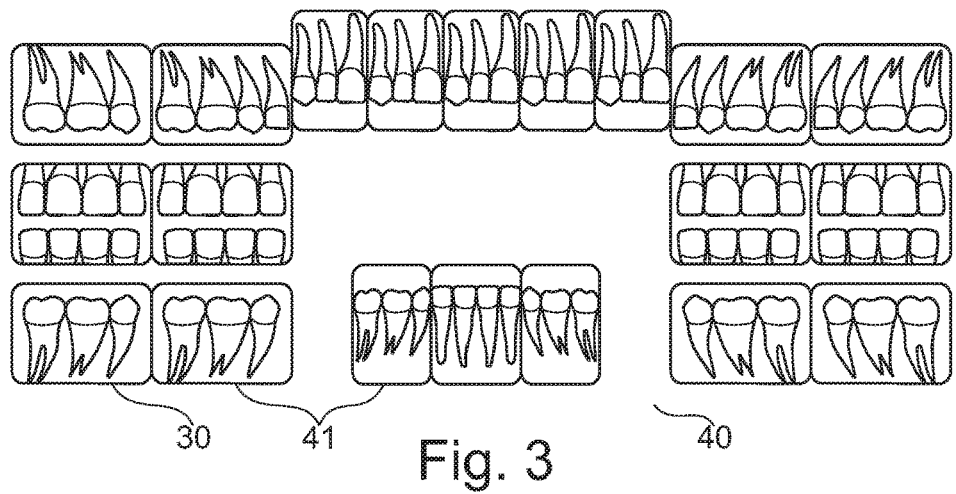
FIG. 3 is a diagrammatical representation of an array of a plurality of projection images of the entire oral cavity of a patient.

FIG. 3 is a diagrammatical representation of an array 40 of a plurality of projection images of the mandibular arch 5 and the maxillary arch 6 of the entire oral cavity of the patient illustrated in FIG. 1. The generated projection image 30, as shown in FIG. 2, can be seen bottom left in FIG. 3. The remaining projection images 41 are generated accordingly from the other sub-volumes 8, 12, 15 illustrated in FIG. 1 and additional sub-volumes of the maxillary arch 6 that are not shown in FIG. 1. The sub-volumes for generating the projection images 30, 41 as shown in FIG. 3 partially overlap each other. The array 40 of the generated intraoral images 30, 41 as shown in FIG. 3 is produced according to a predefined schema, namely the so-called "full mouth series". The projection images 30, 41 can alternatively be generated according to another, arbitrary schema. It is equally possible to generate projection images in the direction of the course 21 of the lower jawbone or of the upper jawbone 6 so that the regions between the teeth are imaged on such a projection image.

Figures 4A, 4B, 4C:
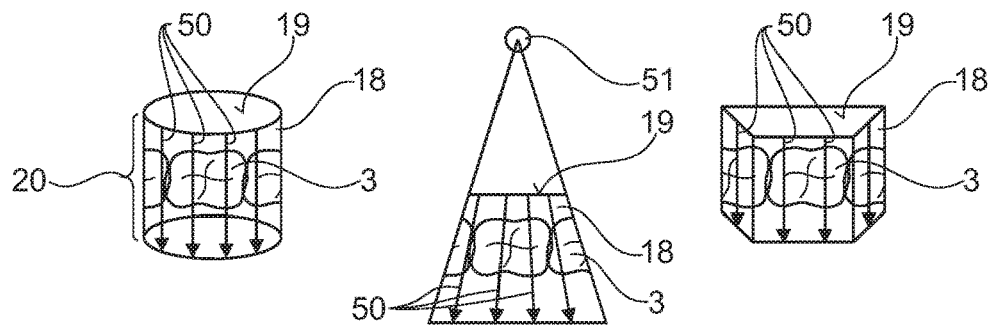
FIG. 4A is a diagrammatical representation of a sub-volume with parallel rays.
FIG. 4B is a diagrammatical representation of an alternative sub-volume in the form of a conical fan.
FIG. 4C is a diagrammatical representation of an alternative sub-volume with a trapezoidal basal surface.

FIG. 4A shows a sub-volume 18 comprising one molar tooth 3 in its entirety and parts of two adjacent teeth, the basal surface 19 being in the form of a circle, the thickness 20 of which being such that the molar teeth 3 are completely enclosed in the sub-volume 18. During generation of the projection image from the sub-volume 18, summation occurs along the virtual X-ray imaging direction represented by virtual parallel rays 50.

FIG. 4B shows the sub-volume 18, as shown in FIG. 4A, the only difference being that the rays 50 extend in the form of a conical fan starting from a virtual X-ray source 51, and the basal surface 19 is in the form of a rectangle.

FIG. 4C shows another alternative embodiment of the sub-volume 18 having a trapezoidal basal surface 19, the X-ray imaging direction being represented by parallel rays 50.

Figure 5:
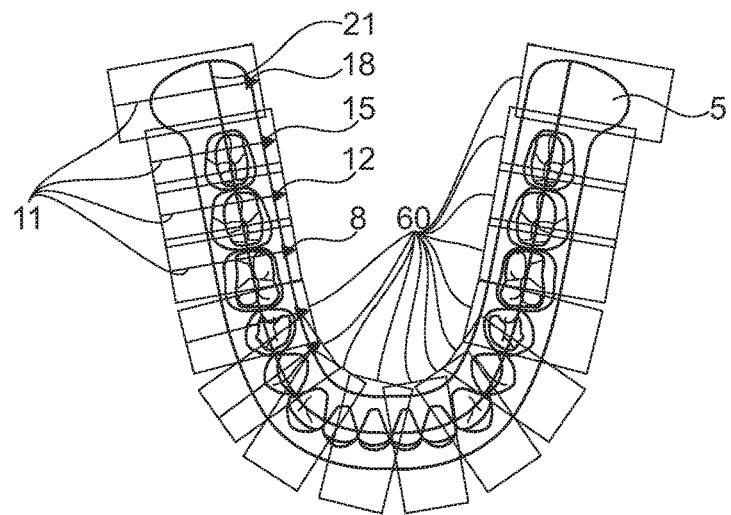
FIG. 5 shows a schema including a plurality of selected sub-volumes.

FIG. 5 is a top view of a schema of a mandibular arch 5 comprising the selected sub-volumes 18, 15, 12, 8 as shown in FIG. 1 and additional sub-volumes 60 disposed in the X-ray imaging direction 11 oriented at right angles to the course 21 of the mandibular arch 5. During generation of the individual projection images, summation occurs in the manner shown in FIG. 4A or FIG. 4C along the parallel virtual rays. Unlike FIG. 1, the individual sub-volumes 18, 15, 12, 8 are selected so as to overlap each other so that portions of the mandibular arch 5 are included not only in a sub-volume but also in its adjacent sub-volume, so that the same portion of the mandibular arch 5 is visible in the projection images generated from these adjacent sub-volumes.

Figure 6:
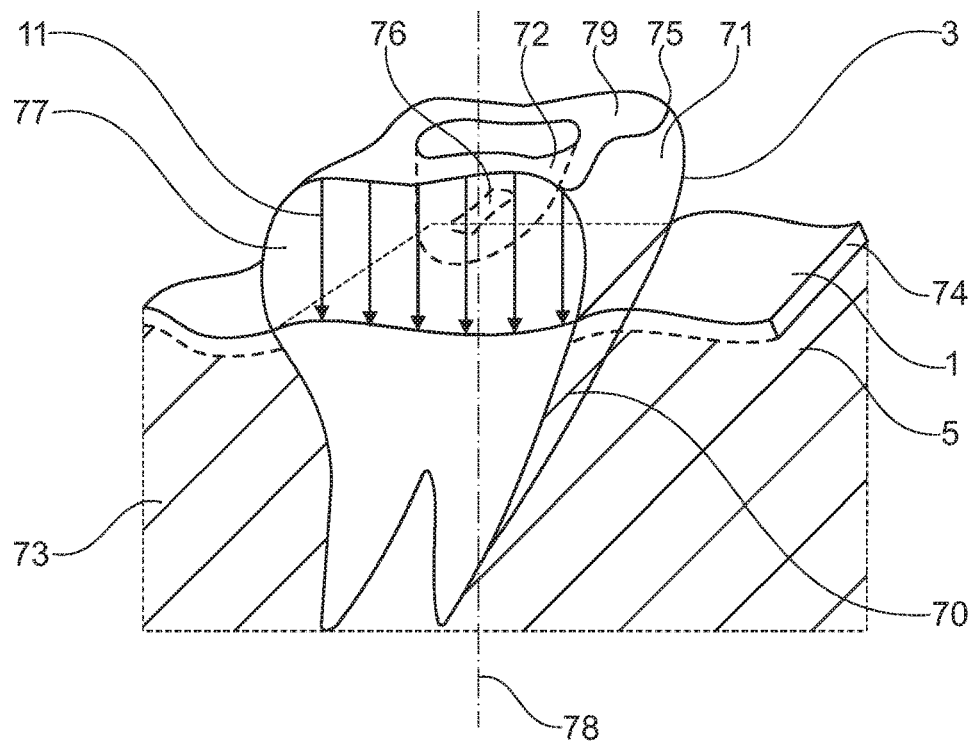
FIG. 6 is a diagrammatical representation of a detail of the 3D volume comprising a single molar tooth.

FIG. 6 is a schema of a detail of the 3D volume 1 including a single molar tooth 3 of the mandibular arch 5. The molar tooth 3 consists of a tooth root 70 and a tooth crown 71 provided with a filling 72. The tooth root 70 is disposed in the jawbone 73. The gingiva 74 covers the jawbone 73. Secondary caries 76 has developed on the reverse side 75 of the filling 72 and is to be diagnosed. A sub-volume 77 is defined by the user or automatically with the assistance of a computer, which sub-volume 77 comprises the tooth crown 71, while the unwanted object, namely the filling 72, is excluded virtually. The remaining sub-objects, such as the tooth root 70, the gingiva 74, and the jawbone 73, that are of no diagnostic significance are likewise omitted when the sub-volume 77 is being defined. The virtual X-ray imaging direction 11 of the volume 77 extends along a tooth axis in the occlusal direction at right angles to the occlusal surface 79. The secondary caries 76 can be better diagnosed by means of the projection image generated from the sub-volume 77 in the X-ray imaging direction 11, due to the fact that the filling 72 has been excluded virtually. The filling can alternatively be excluded by means of a specific function. Such a function is designed such that the portions, such as a filling, that are of no significance for evaluation purposes are made invisible or weakly visible, while those portions, such as carious regions, that are significant for evaluation purposes are highlighted in the image.

Figure 7:
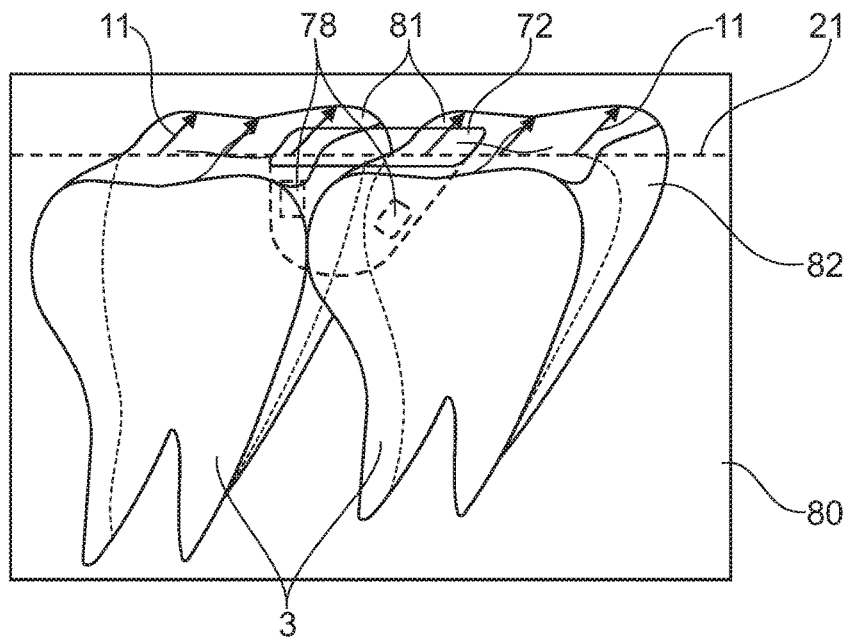
FIG. 7 is a diagrammatical representation of an alternative detail comprising a filling between two molar teeth.

FIG. 7 is a schema of a detail of the 3D volume 1 as shown in FIG. 6, except that the filling 72 is disposed between two molar teeth 3 and the X-ray imaging direction 11 is oriented in the lingual direction at right angles to the course 21 of the mandibular arch 5.

FIG. 7 shows a section plane 80 that passes through the center of the two molar teeth 3. The sub-volume 81 is formed by the section plane 80 and the external contour 82 of the rear surface of the molar teeth 3. This improves the diagnosis of the secondary caries 78 on the reverse side of the filling 72 using the projection image generated from the sub-volume 81 in the X-ray imaging direction 11.

LIST OF REFERENCE NUMERALS OR CHARACTERS 1 3D volume
2 front incisal teeth
3 lateral molar teeth
4 maxillary arch
5 mandibular arch
6 upper jawbone
7 lower jawbone
8 virtual sub-volume
9 basal surface
10 thickness
11 X-ray imaging direction
12 second sub-volume
13 basal surface
14 thickness
15 third sub-volume
16 basal surface
17 thickness
18 fourth sub-volume
19 basal surface
20 thickness
21 course
30 projection image
3 0 arrangement
41 projection image
50 rays
60 further sub-volumes

The invention claimed is:

1. A method for creating a plurality of virtual projection images of dental structures, the method comprising:
defining a plurality of sub-volumes within an image volume represented by volumetric image data, wherein at least one sub-volume includes at least one tooth and an unwanted object within the at least one tooth, and wherein each sub-volume partially overlaps another sub-volume; and
simulating transmission of x-rays through each of the plurality of sub-volumes using volumetric image data for each sub-volume to generate a plurality of virtual projection images, wherein a simulated x-ray transmission direction is different for each of the plurality of sub-volumes, and wherein for the at least one sub-volume that includes the unwanted object within the at least one tooth, volumetric image data corresponding to the unwanted object within the at least one tooth is weighted less than volumetric image data corresponding to the at least one tooth.

2. The method as defined in claim 1, wherein the volumetric image data are x-ray absorption values.

3. The method as defined in claim 1, wherein the simulated transmission of x-rays through a sub-volume is performed by summing elements of the volumetric image data for the sub-volume that are successively disposed along the simulated x-ray transmission direction for the sub-volume.

4. The method as defined in claim 1, further comprising:
segmenting the volumetric image data to identify the at least one tooth and the unwanted object within the at least one tooth.

5. The method as defined in claim 2, wherein the volumetric image data corresponding to the unwanted object within the at least one tooth is weighted less by decreasing the magnitude of the x-ray absorption values corresponding to the unwanted object within the at least one tooth.

6. The method as defined in claim 4, wherein an outer contour of the at least one sub-volume, that includes the identified at least one tooth, is defined so as to correspond to an outer contour of the at least one tooth.

7. The method as defined in claim 1, wherein each of the plurality of sub-volumes includes a basal surface and the simulated x-ray transmission direction for each sub-volume is substantially orthogonal to the basal surface.

8. The method as defined in claim 1, further comprising:
segmenting the volumetric image data to determine positions and orientations of plurality of teeth in a dental arch.

9. The method as defined in claim 8, wherein the plurality of sub-volumes are defined based on the determined positions and orientations of the plurality of teeth in the dental arch such that each sub-volume includes a portion of at least one tooth.

10. The method as defined in claim 1, wherein the plurality of virtual projection images are generated according to a predefined schema and displayed, on a display unit, in accordance with the predefined schema.

11. The method as defined in claim 1, wherein each sub-volume is defined by (i) defining a basal surface of the sub-volume and (ii) defining a thickness of the sub-volume in a direction orthogonal to the basal surface of the sub-volume,
wherein a shape of the basal surface is one of: circular, rectangular, or trapezoidal.

12. The method as defined in claim 11, wherein a volume of space, defined by an area of a basal surface of the at least one sub-volume and a thickness of the at least one sub-volume in the simulated x-ray transmission direction, entirely includes the at least one tooth.

13. The method as defined in claim 1, wherein each virtual projection image represents a total amount of x-ray attenuation through a corresponding sub-volume along the simulated x-ray transmission direction.

14. The method as defined in claim 1, wherein the simulating transmission of x-rays through each of the plurality of sub-volumes includes a simulation of at least one of the following factors applicable to generating a conventional intraoral image: X-ray scattering, X-ray detector efficiency, X-ray detector sensitivity, and a relative position between an X-ray detector and an X-ray source.

15. The method as defined in claim 1, wherein the plurality of sub-volumes are arranged in a partially overlapping manner in a direction of a dental arch.

16. The method as defined in claim 1, wherein the plurality of sub-volumes are arranged in a partially overlapping manner so as to follow a curvature of a dental arch.

17. The method of claim 1, wherein the plurality of virtual projection images lie in different two-dimensional flat planes.

18. A method for creating a plurality of virtual projection images of dental structures, the method comprising:
defining a plurality of sub-volumes within an image volume represented by volumetric image data, wherein at least one sub-volume includes at least one tooth, and wherein each sub-volume partially overlaps another sub-volume; and
simulating transmission of x-rays through each of the plurality of sub-volumes using volumetric image data for each sub-volume to generate a plurality of virtual projection images, wherein a simulated x-ray transmission direction is different for each of the plurality of sub-volumes, and wherein volumetric image data corresponding to a part of the at least one tooth is weighed less than volumetric image data corresponding to another part of the at least one tooth.

19. The method as defined in claim 18, wherein the plurality of sub-volumes are arranged in a partially overlapping manner in a direction of a dental arch.

20. The method as defined in claim 18, wherein the plurality of sub-volumes are arranged in a partially overlapping manner so as to follow a curvature of a dental arch.

21. The method as defined in claim 18, wherein the simulating transmission of x-rays through a sub-volume is performed by summing elements of the volumetric image data for the sub-volume that are successively disposed along the simulated x-ray transmission direction for the sub-volume, and
wherein the simulated x-ray transmission direction for each sub-volume is substantially orthogonal to a basal surface of the sub-volume.

22. The method as defined in claim 18, wherein the plurality of virtual projection images are generated according to a predefined schema and displayed, on a display unit, in accordance with the predefined schema.

23. The method as defined in claim 18, further comprising:
segmenting the volumetric image data to determine positions and orientations of one or more teeth in a dental arch.

24. The method as defined in claim 23, wherein the plurality of sub-volumes are defined based on the determined positions and orientations of the one or more teeth in the dental arch such that each sub-volume includes a portion of at least one tooth.

* * * * *